US008278237B2

(12) United States Patent
Yamada et al.

(10) Patent No.: US 8,278,237 B2
(45) Date of Patent: Oct. 2, 2012

(54) CATALYST FOR AROMATIZATION OF LOWER HYDROCARBONS AND PROCESS FOR PRODUCTION OF AROMATIC COMPOUNDS

(75) Inventors: Shinichi Yamada, Mishima (JP); Tomohiro Yamada, Numazu (JP); Yuji Ogawa, Kawagoe (JP); Hirokazu Akiyama, Izunokuni (JP); Takuya Hatagishi, Numazu (JP)

(73) Assignee: Meidensha Corporation, Tokyo (JP)

( * ) Notice: Subject to any disclaimer, the term of this patent is extended or adjusted under 35 U.S.C. 154(b) by 401 days.

(21) Appl. No.: 12/524,029

(22) PCT Filed: Feb. 13, 2008

(86) PCT No.: PCT/JP2008/052284
§ 371 (c)(1),
(2), (4) Date: Jul. 22, 2009

(87) PCT Pub. No.: WO2008/114550
PCT Pub. Date: Sep. 25, 2008

(65) Prior Publication Data
US 2010/0016647 A1 Jan. 21, 2010

(30) Foreign Application Priority Data

Mar. 20, 2007 (JP) ................................. 2007-073470
Nov. 12, 2007 (JP) ................................. 2007-293010
Nov. 12, 2007 (JP) ................................. 2007-293011

(51) Int. Cl.
*B01J 29/06* (2006.01)
*C07C 2/52* (2006.01)
*C07C 15/00* (2006.01)

(52) U.S. Cl. .............. 502/77; 502/87; 502/244; 502/60; 502/62; 502/63; 502/64; 502/71; 502/73; 585/407; 585/408; 585/409; 585/410; 585/411; 585/418; 585/420

(58) Field of Classification Search .................... 502/60, 502/62, 63, 64, 71, 73, 77, 244; 585/407, 585/408, 409, 410, 411, 418, 420
See application file for complete search history.

(56) References Cited

U.S. PATENT DOCUMENTS

| 4,100,262 A * | 7/1978 | Pelrine ........................... 423/703 |
| 4,543,347 A * | 9/1985 | Heyward et al. ................. 502/61 |
| 6,051,520 A | 4/2000 | Wu et al. |
| 2010/0137666 A1 | 6/2010 | Yamada et al. |

FOREIGN PATENT DOCUMENTS

| JP | 7-000826 A | 1/1995 |
| JP | 10-024237 A | 1/1998 |
| JP | 10-128123 A | 5/1998 |
| JP | 10-272366 A | 10/1998 |
| JP | 11-060514 A | 3/1999 |
| JP | 2002-336704 A | 11/2002 |
| JP | 2004-269398 A | 9/2004 |
| JP | 2007-014894 A | 1/2007 |

OTHER PUBLICATIONS

S. Qi et al., "Methane aromatization using Mo-based catalysts prepared by microwave heating," Catalysis Today, vol. 98, No. 4, 2004, pp. 639-645.
F. Solymosi et al., "Aromatization of Methane over Supported and Unsupported Mo-Based Catalysts," Journal of Catalysis, vol. 165, Article No. CA971478, 1997, pp. 150-161.
Satoshi Kikuchi et al., Study on Mo/HZSM-5 Catalysts Modified by Bulky Aminoalkyl-Substituted Silyl Compounds for The Selective Methane-to-Benzene (MTB) Reaction, Journal of Catalysis, vol. 242, 2006, pp. 349-356.
Qun Dong et al., "Studies on Mo/HZSM-5 Complex Catalyst for Methane Aromatization", Journal of Natural Gas Chemistry, vol. 13 (2004), pp. 36-40.
USPTO Office Action, U.S. Appl. No. 12/595,924, U.S. Appl. No. 11/232,011, 5 pages.

* cited by examiner

*Primary Examiner* — Elizabeth Wood
(74) *Attorney, Agent, or Firm* — Foley & Lardner LLP (57) ABSTRACT

A catalyst for producing aromatic compounds from lower hydrocarbons while improving activity life stability of methane conversion rate; benzene formation rate; naphthalene formation rate; and total formation rate of benzene, toluene and xylene is formed by loading molybdenum and copper on metallo-silicate serving as a substrate and then calcining the metallo-silicate. When the catalyst is reacted with a reaction gas containing lower hydrocarbons and carbonic acid gas, aromatic compounds are produced. In order to obtain the catalyst, it is preferable that molybdenum and copper are loaded on zeolite formed of metallo-silicate after the zeolite is treated with a silane compound larger than a pore of the zeolite in diameter and having an amino group and a straight-chain hydrocarbon group, the amino group being able to selectively react with the zeolite at a Bronsted acid point of the zeolite. It is preferable that a loaded amount of molybdenum is within a range of from 2 to 12 wt. % based on total amount of the calcined catalyst while copper is loaded at a copper to molybdenum molar ratio of 0.01 to 0.8.

13 Claims, 9 Drawing Sheets

CATALYST FOR AROMATIZATION OF LOWER HYDROCARBONS AND PROCESS FOR PRODUCTION OF AROMATIC COMPOUNDS

BACKGROUND OF THE INVENTION

The present invention relates to an advanced use of natural gas, biogas and methane hydrate which contain methane as a main component. Natural gas, biogas and methane hydrate are regarded as effective energy resources against global warming, and therefore an interest in techniques using them has grown. A methane resource is expected to be a novel organic resource in the next generation or to be a hydrogen resource for use in fuel cells, by putting a clean characteristic of methane to full use. More particularly, the present invention relates to: a catalyst chemistry conversion technique for efficiently producing aromatic compounds exemplified by benzene and naphthalene which are materials of chemical products such as plastics, and high purity hydrogen, from methane; and a method for producing the catalyst.

SUMMARY OF THE INVENTION

As a method for producing hydrogen and aromatic compounds such as benzene from methane, a method of reacting methane in the presence of a catalyst is known. It is generally said that molybdenum loaded on a ZSM-5 based zeolite is effectively used as such a catalyst (Non-patent document 1). However, even in the case of using such a catalyst, there are problems such as heavy precipitation of carbon and low methane conversion rate.

In order to solve the problems, a catalyst is proposed, for example, in Patent documents 1 to 3, the catalyst being formed by loading catalyst materials such as Mo (molybdenum) on a porous metallo-silicate. It is confirmed by Patent documents 1 to 3 that lower hydrocarbons efficiently become aromatic compounds when using a catalyst produced such that a metal component is loaded on a porous metallo-silicate formed with pores of 7 angstrom in diameter and serving as a substrate, with which hydrogen is obtained at high purity. According to the above patent documents, the substrate loads the metal component exemplified by molybdenum, cobalt, iron and the like. Further, a catalyst disclosed in Patent document 4 is to produce aromatic compounds from lower hydrocarbons, and is formed by treating zeolite formed of metallo-silicate with silane compounds and then loading molybdenum thereon. With this aromatic compounds-producing catalyst, a rate of producing a certain aromatic compound such as benzene and toluene can be stabilized.

As a method for producing hydrogen and aromatic compounds such as benzene from methane, a method of reacting methane in the presence of a catalyst formed such that molybdenum is loaded on ZSM-5 is known as an effective one.

However, even in the case of using this catalyst, precipitation of carbon is heavy. This carbon precipitation deteriorates a catalytic performance in a short time. Additionally, a methane conversion rate (a rate of consuming methane used for producing aromatic compounds and hydrogen) is low. The catalyst as disclosed in Patent documents 1 to 3 cannot sufficiently solve the problems, and therefore it is desired to develop a catalyst further excellent in efficiency of aromatic compound production.

For utilization of a catalyst which can reform methane into benzene, it is necessary to improve the methane conversion rate. Then, it is required for improving the methane conversion rate to increase a reaction temperature at the occasion of introducing methane gas. In the catalyst as disclosed in Patent documents 1 to 3, an activity life of the catalyst is significantly shortened with increase of the temperature at which the catalyst is reacted with a raw material.

The rate of aromatic compound production can be improved with the catalyst as disclosed in Patent document 4; however, a further improvement is desired concerning an activity life stability of the methane formation rate, benzene formation rate, naphthalene formation rate and BTX formation rate (or a total formation rate of benzene, toluene and xylene) from the viewpoint of mass production of aromatic compounds.

Non-patent document 1: "JOURNAL OF CATALYSIS" 1997, vol. 165, pp. 150-161

Patent document 1: Japanese Patent Provisional Publication No. 10-272366

Patent document 2: Japanese Patent Provisional Publication No. 11-60514

Patent document 3: Japanese Patent Provisional Publication No. 2004-269398

Patent document 4: Japanese Patent Provisional Publication No. 2007-14894

DISCLOSURE OF INVENTION

In view of the above, a catalyst for solving the problems and for producing an aromatic compound from a lower hydrocarbon includes a metallo-silicate serving as a substrate and calcined upon loading molybdenum and copper on the metallo-silicate, in which the aromatic compound is produced by reacting the catalyst with the lower hydrocarbon and a carbonic acid gas.

Additionally, a method for solving the problems and for producing an aromatic compound includes the steps of loading molybdenum and copper on metallo-silicate serving as a substrate; calcining the metallo-silicate upon loading molybdenum and copper thereon; and reacting the catalyst with a reaction gas containing a lower hydrocarbon and a carbonic acid gas to produce the aromatic compound.

According to the catalyst for producing aromatic compounds from lower hydrocarbons, an activity life stability of a methane conversion rate, a benzene formation rate, a naphthalene formation rate and a BTX formation rate (or a total formation rate of benzene, toluene and xylene) is improved. In order to produce aromatic compounds, the carbonic acid gas may be replaced with carbon monoxide gas. An addition amount of the carbonic acid gas is preferably within a range of from 0.5 to 6 wt. % based on the total of the reaction gas. With this, the activity life stability of the methane conversion rate, the benzene formation rate, the naphthalene formation rate and the BTX formation rate is reliably improved.

In order to obtain the catalyst for producing aromatic compounds from lower hydrocarbons, it is preferable that molybdenum and copper are loaded on zeolite formed of metallo-silicate after the zeolite is treated with a silane compound larger than a pore of the zeolite in diameter and having an amino group and a straight-chain hydrocarbon group, the amino group being able to selectively react with the zeolite at a Bronsted acid point of the zeolite.

The metallo-silicate is a porous metallo-silicate formed with pores of 4.5 to 6.5 angstrom in diameter, and exemplified by ZSM-5 and MCM-22.

The silane compound is exemplified by APTES (3-aminoproxyl-triethoxysilane). A modification treatment with the silane compound is preferably made in such a manner that an addition amount of the silane compound of after calcination is less than 2.5 wt. %, for example, 0.5 wt. % based on total amount of the catalyst. With this, the activity life stability of the methane conversion rate, the benzene formation rate, the naphthalene formation rate and the BTX formation rate is reliably improved.

A loaded amount of molybdenum is preferably within a range of from 2 to 12 wt. % based on total amount of the calcined catalyst while copper is loaded at a copper to molybdenum molar ratio of 0.01 to 0.8. With this, the activity life stability of the methane conversion rate, the benzene formation rate, the naphthalene formation rate and the BTX formation rate is reliably improved.

A calcining temperature applied during the calcination made after molybdenum and copper are loaded on the metallo-silicate is preferably within a range of from 550 to 800° C. When the carbonic acid gas is not enough (or is less than 0.5%), an oxidation action of precipitated coke is decreased so as to decrease the activity life stability. On the other hand, when the carbonic acid gas is excessive (or is not less than 6%), hydrogen and carbon monoxide is excessively produced by a direct oxidation reaction of methane gas so as to lower a methane gas concentration required to make the reaction, thereby decreasing a produced amount of benzene. An addition amount of the carbonic acid gas is therefore set within a range of from 0.5 to 6%. With this, the methane conversion rate, the benzene formation rate, the naphthalene formation rate and the BTX formation rate are efficiently stabilized.

According to the invention as discussed above, the activity life stability of the methane conversion rate, the benzene formation rate, the naphthalene formation rate and the BTX formation rate (or the total formation rate of benzene, toluene and xylene) is improved. Therefore, a produced amount of useful aromatic compounds such as benzene and toluene is increased.

DETAILED DESCRIPTION OF THE INVENTION

A catalyst for producing aromatic compounds from lower hydrocarbons, according to the present invention contains at least one selected from the group consisting of molybdenum and compounds thereof. At the production of aromatic compounds, the catalyst for producing aromatic compounds from lower hydrocarbons is reacted with carbon dioxide in addition to lower hydrocarbons.

The catalyst for producing aromatic compounds from lower hydrocarbons is formed by treating zeolite formed of metallo-silicate with, a silane compound larger than a pore of the zeolite in diameter and having an amino group and a straight-chain hydrocarbon group, the amino group being able to selectively react with the zeolite at a Bronsted acid point of the zeolite, and then by loading molybdenum and copper on the zeolite.

A substrate on which the above-mentioned metal component is loaded includes a porous metallo-silicate substantially formed with pores of 4.5 to 6.5 angstrom in diameter. The metallo-silicate is treated to be modified with silane and then immersed in an impregnation solution prepared with ammonium molybdate and copper acetate or copper sulfate, so as to be impregnated with a molybdenum component and a copper component. The metallo-silicate is then dried and calcined, thereby loading the molybdenum component and the copper component thereon.

As the above-mentioned catalyst for producing aromatic compounds from lower hydrocarbons, catalyst can obtain stability when the molybdenum component and the copper component are loaded on metallo-silicate treated with a silane component to be modified with silane. Particularly, an activity life stability of: a methane conversion rate; a benzene formation rate; naphthalene formation rate; and a BTX formation rate (or a total formation rate of benzene, toluene and xylene) is improved.

Referring to the following Examples, the catalyst for producing aromatic compounds from lower hydrocarbons will be discussed.

1. Production of Catalyst for Producing Aromatic Compounds from Lower Hydrocarbons (Hereinafter Abbreviated as "a Catalyst")

Comparative Example 1

An ammonium type ZSM-5 ($SiO_2/Al_2O_3$=25 to 70) was employed as a metallo-silicate. Molybdenum alone was loaded on the metallo-silicate, thereby obtaining a catalyst of Comparative Example 1.

(1) Preparation

Preparation of an inorganic component: ZSM-5 (82.5 wt. %), clay (12.5 wt. %), and glass fiber (7 wt. %)

Total Preparation: the above-mentioned inorganic component (76.5 wt. %), an organic binder (17.3 wt. %), and water content (7 wt. %)

(2) Shaping

The inorganic component, the organic binder and water content were prepared in the above-mentioned preparation ratio and then mixed or kneaded by a means of kneading (a kneader). Subsequently, the thus mixed substance was shaped by a vacuum extrusion machine into a rod (5 mm in diameter and 10 mm in length). An extrusion pressure applied during this shaping process was set within a range of from 2 to 8 MPa.

(3) Impregnation of Molybdenum

The shaped substance obtained by the above-mentioned shaping process was immersed in a stirred ammonium molybdate solution so as to be impregnated with a molybdenum component, followed by drying and calcining processes as will be discussed. The shaped substrate was added such that molybdenum was to be in an amount of 6 wt. % based on the total amount of calcined catalyst.

(4) Drying and Calcining Catalyst

In order to eliminate the water content added in the shaping process, a drying process was carried out at 70° C. for about 12 hours. A calcining temperature during the calcining process was set within a range of from 550 to 800° C. in air. That is because a temperature of not higher than 550° C. causes a substrate to decrease in strength while a temperature of not lower than 800° C. causes the substrate to decrease in property (or activity). Temperature-increasing and temperature-decreasing rates in the calcining process were set within a range of from 90 to 100° C./hour. During the calcining process, a temperature-keeping over 2 to 6 hours was carried out twice within a range of from 250 to 450° C. in order not to instantaneously calcine the organic binder added in the shaping process, thereby removing the binder. This is based on a reason that the binder calcines instantaneously to decrease the strength of the calcined substrate when the temperature-increasing rate and the temperature-decreasing rate exceed the above-mentioned rate and when time for the temperature-keeping is not taken.

(5) Carburization Treatment

The above-mentioned calcined substrate was increased in temperature to 700° C. within 1 hour under the flow of a mixture gas of $CH_4$ and $H_2$. This condition was kept for 3 hours. Thereafter, the catalyst was increased in temperature to 780° C. upon replacing the atmosphere with that of a reaction gas formed of $CH_4$.

Comparative Example 2

A catalyst as Comparative Example 2 was formed loading molybdenum and cobalt thereon. It was produced by the same preparation and the same producing process (including the shaping process, the drying process, the calcining process and the carburization treatment) as the catalyst of Comparative Example 1, with the exception of the impregnation process.

In this impregnation process, an impregnation solution prepared with cobalt acetate and ammonium molybdate was stirred. Then, the substrate shaped in the shaping process as discussed in Comparative Example 1 was immersed in the stirred impregnation solution, thereby impregnating the shaped substrate with a molybdenum component and a cobalt component. This substrate was dried and then calcined in air, thereby obtaining a ZSM-5 substrate loading molybdenum and cobalt. In preparation of the impregnation solution, a loaded amount of molybdenum was set to be 6 wt. % based on the total amount of calcined substrate, while a loaded amount of cobalt was set to have a cobalt to molybdenum molar ratio of 0.3:1.0.

Comparative Example 3

A catalyst as Comparative Example 2 was formed loading molybdenum and iron thereon. It was produced by the same producing process (including the shaping process, the drying process, the calcining process and the carburization treatment) as the catalyst of Comparative Example 1, with the exception of the impregnation process.

In this impregnation process, an impregnation solution prepared with iron acetate and ammonium molybdate was stirred. Then, the substrate shaped in the shaping process as discussed in Comparative Example 1 was immersed in the stirred impregnation solution, thereby impregnating the shaped substrate with a molybdenum component and a ferrous component. This substrate was dried and then calcined in air, thereby obtaining a ZSM-5 substrate loading molybdenum and iron. In preparation of the impregnation solution, a loaded amount of molybdenum was set to be 6 wt. % based on the total amount of calcined substrate, while a loaded amount of iron was set to have a iron to molybdenum molar ratio of 0.3:1.0.

Example 1

A catalyst as Example 1 was formed loading molybdenum and copper thereon. It was produced by the same producing process (including the shaping process, the drying process, the calcining process and the carburization treatment) as the catalyst of Comparative Example 1, with the exception of the impregnation process.

In this impregnation process, an impregnation solution prepared with copper acetate and ammonium molybdate was stirred. Then, the substrate shaped in the shaping process as discussed in Comparative Example 1 was immersed in the stirred impregnation solution, thereby impregnating the shaped substrate with a molybdenum component and a copper component. This substrate was dried and then calcined in air, thereby obtaining a ZSM-5 substrate loading molybdenum and copper. In preparation of the impregnation solution, a loaded amount of molybdenum was set to be 6 wt. % based on the total amount of calcined substrate, while a loaded amount of copper was set to have a copper to molybdenum molar ratio of 0.3:1.0.

2. Evaluation of Catalysts of Comparative Examples and Examples

A method for evaluating the catalysts of Comparative Examples and Examples will be discussed.

14 g of a catalyst (having a zeolite ratio of 82.50%) serving as a target for evaluation was charged into a reaction pipe of a fixed-bed flow reactor (the pipe had an internal diameter of 18 mm and was produced in such a manner as to make a calorizing treatment on Inconel 800H's portion with which gas is to be brought into contact). Then, each reaction gas was supplied to the reaction pipe. The catalyst was thus reacted with the reaction gas under the conditions of: 3000 ml/g-ZSM-5/h ($CH_4$ gas flow base) of reaction space velocity; 780° C. of reaction temperature; 24-hour reaction time; and 0.3 MPa of reaction pressure. During the reaction, a product analysis was conducted to examine a time variation in a methane conversion rate, a hydrogen formation rate, a benzene formation rate, a naphthalene formation rate, a BTX formation rate and a carbon formation rate. The product analysis was carried out by using TCD-GC and FID-GC.

The followings are definitions of the methane conversion rate, the hydrogen formation rate, the benzene formation rate, the naphthalene formation rate, the BTX formation rate and the carbon formation rate:

Methane conversion rate=(a flow rate of raw material methane−a flow rate of unreacted methane)/the flow rate of raw material methane×100;

Benzene formation rate="the number of nmol of benzene produced by 1 g of the catalyst per second";

Naphthalene formation rate="the number of nmol of naphthalene produced by 1 g of the catalyst per second";

BTX formation rate="the total number of nmol of benzene, toluene and xylene produced by 1 g of the catalyst per second"; and Carbon formation rate="the number of nmol of carbon produced by 1 g of the catalyst per second".

Figure 1:
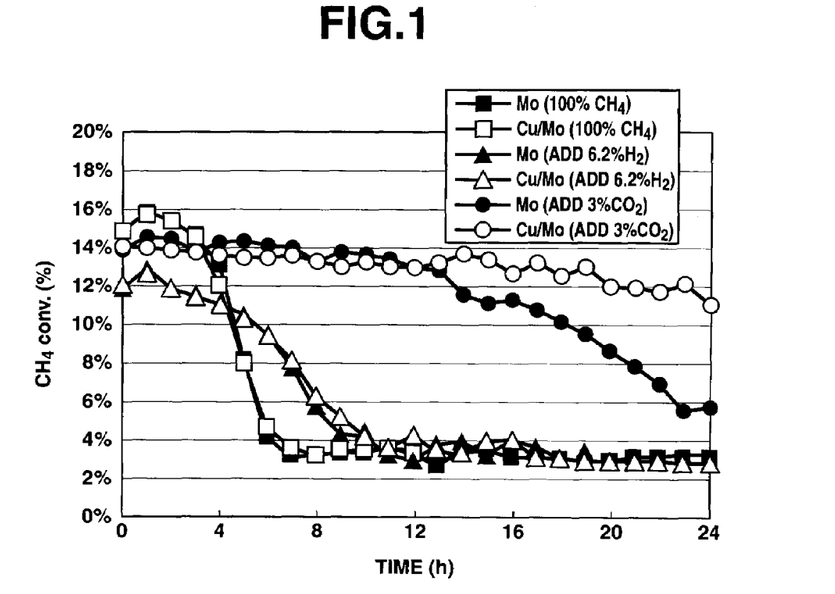
FIG. 1 is a graph showing a time variation in a methane conversion rate, in which each of a catalyst (Mo) relating to Comparative Example 1 and a catalyst (Cu/Mo) relating to Example 1 was reacted with each reaction gas of: a 100% methane gas ($CH_4$); a methane gas to which 6% hydrogen ($H_2$) was added (Add) to have a methane to hydrogen molar ratio of 100:6.2; and a methane gas to which 3% carbonic acid gas ($CO_2$) was added (Add) to have a methane to carbonic acid gas ($CO_2$) molar ratio of 100:3.

FIG. 1 is a graph showing a time variation in the methane conversion rate, in which each of the catalyst (Mo) relating to Comparative Example 1 and the catalyst (Cu/Mo) relating to Example 1 was reacted with each reaction gas of: a 100% methane gas; a methane gas to which 6% hydrogen was added to have a methane to hydrogen molar ratio of 100:6.2; and a methane gas to which 3% carbonic acid gas was added to have a methane to carbonic acid gas ($CO_2$) molar ratio of 100:3.

Figure 2:
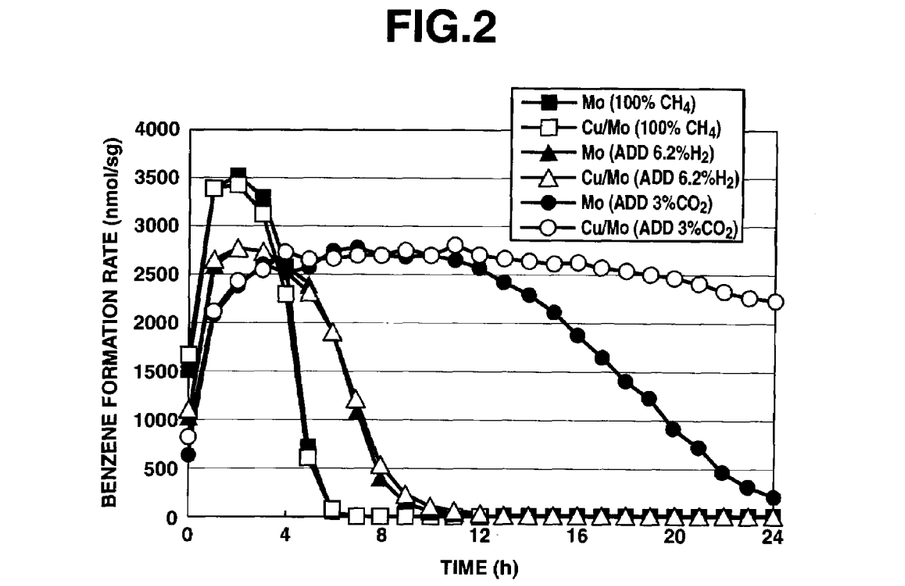
FIG. 2 is a graph showing a time variation in a benzene formation rate, in which each of a catalyst (Mo) relating to Comparative Example 1 and a catalyst (Cu/Mo) relating to Example 1 was reacted with each reaction gas of: a 100% methane gas ($CH_4$); a methane gas to which 6% hydrogen ($H_2$) was added (Add) to have a methane to hydrogen molar ratio of 100:6.2; and a methane gas to which 3% carbonic acid gas ($CO_2$) was added (Add) to have a methane to carbonic acid gas ($CO_2$) molar ratio of 100:3.

FIG. 2 is a graph showing a time variation in the benzene formation rate, in which each of the catalysts relating to Comparative Example 1 and to Example 1 was reacted with each reaction gas of: a 100% methane gas; a methane gas to which 6% hydrogen was added to have a methane to hydrogen molar ratio of 100:6.2; and a methane gas to which 3% carbonic acid gas was added to have a methane to carbonic acid gas ($CO_2$) molar ratio of 100:3.

Figure 3:
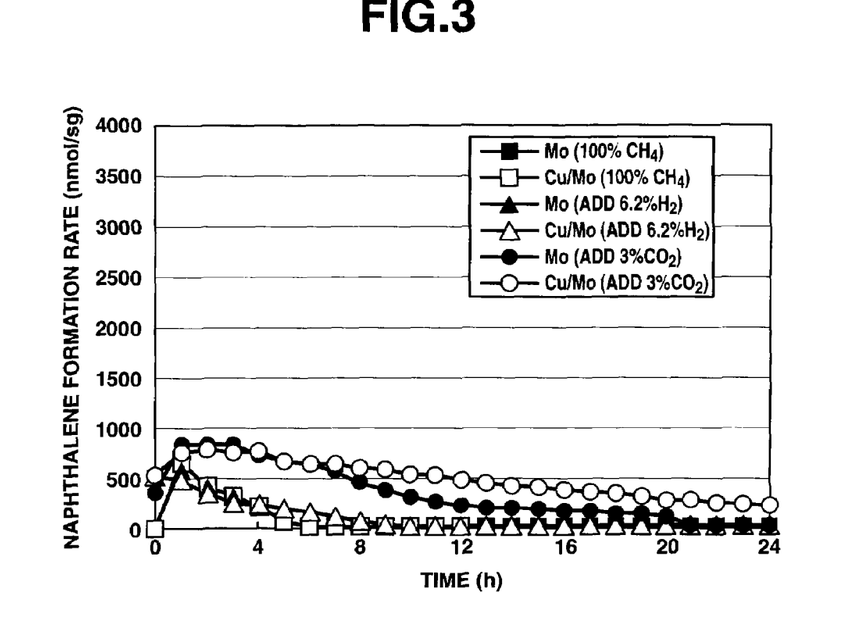
FIG. 3 is a graph showing a time variation in a naphthalene formation rate, in which each of a catalyst (Mo) relating to Comparative Example 1 and a catalyst (Cu/Mo) relating to Example 1 was reacted with each reaction gas of: a 100% methane gas ($CH_4$); a methane gas to which 6% hydrogen ($H_2$) was added (Add) to have a methane to hydrogen molar ratio of 100:6.2; and a methane gas to which 3% carbonic acid gas ($CO_2$) was added (Add) to have a methane to carbonic acid gas ($CO_2$) molar ratio of 100:3.

FIG. 3 is a graph showing a time variation in the naphthalene formation rate, in which each of the catalysts relating to Comparative Example 1 and to Example 1 was reacted with each reaction gas of: a 100% methane gas; a methane gas to which 6% hydrogen was added to have a methane to hydrogen molar ratio of 100:6.2; and a methane gas to which 3% carbonic acid gas was added to have a methane to carbonic acid gas ($CO_2$) molar ratio of 100:3.

Figure 4:
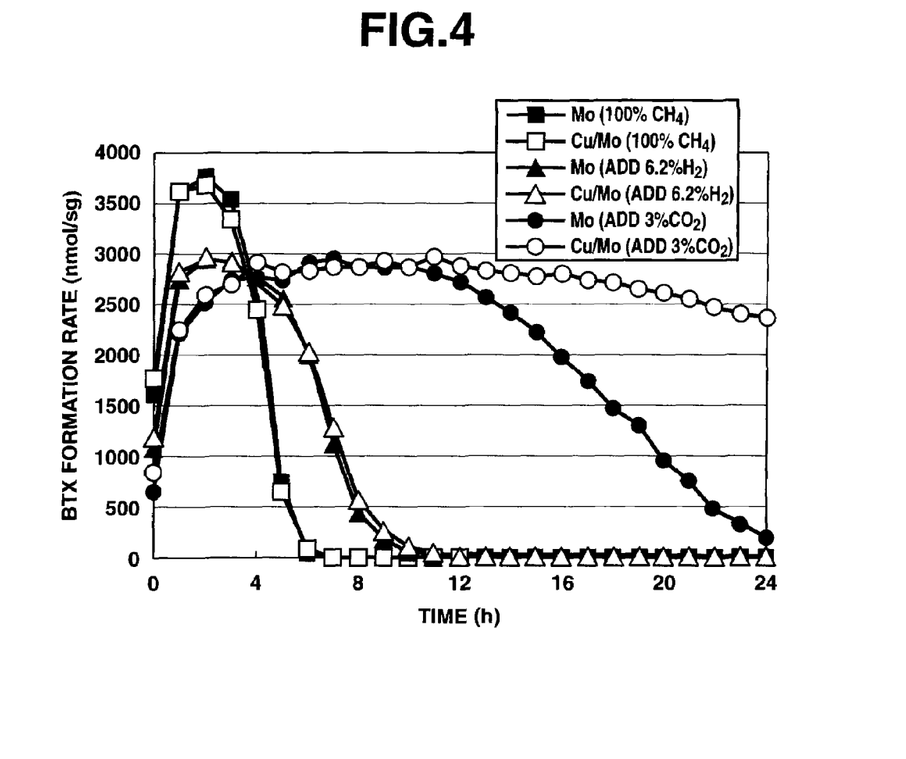
FIG. 4 is a graph showing a time variation in a BTX formation rate, in which each of a catalyst (Mo) relating to Comparative Example 1 and a catalyst (Cu/Mo) relating to Example 1 was reacted with each reaction gas of: a 100% methane gas ($CH_4$); a methane gas to which 6% hydrogen ($H_2$) was added (Add) to have a methane to hydrogen molar ratio of 100:6.2; and a methane gas to which 3% carbonic acid gas ($CO_2$) was added (Add) to have a methane to carbonic acid gas ($CO_2$) molar ratio of 100:3.

FIG. 4 is a graph showing a time variation in the BTX formation rate, in which each of the catalysts relating to Comparative Example 1 and to Example 1 was reacted with each reaction gas of: a 100% methane gas; a methane gas to which 6% hydrogen was added to have a methane to hydrogen molar ratio of 100:6.2; and a methane gas to which 3% carbonic acid gas was added to have a methane to carbonic acid gas ($CO_2$) molar ratio of 100:3.

Figure 5:
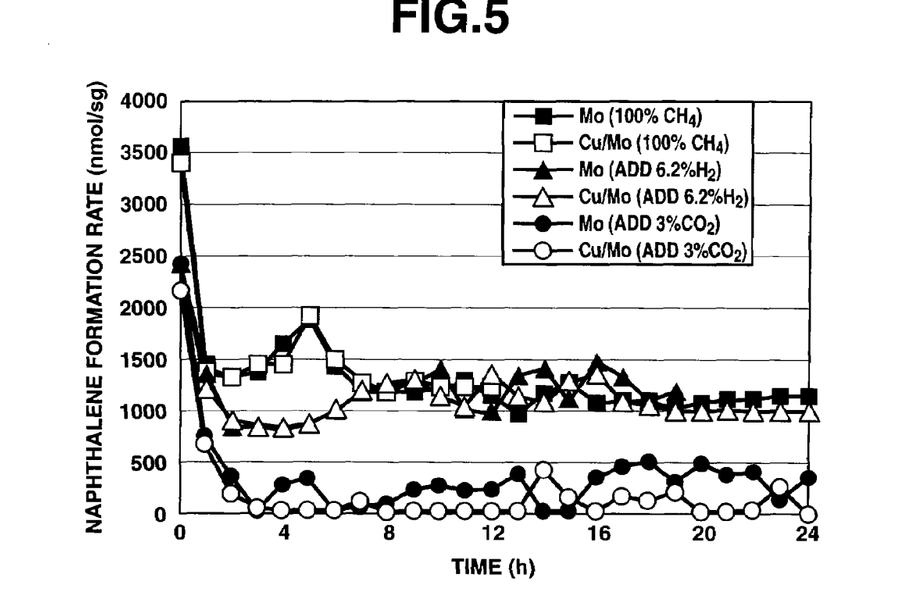
FIG. 5 is a graph showing a time variation in a carbon formation rate, in which each of a catalyst (Mo) relating to Comparative Example 1 and a catalyst (Cu/Mo) relating to Example 1 was reacted with each reaction gas of: a 100% methane gas ($CH_4$); a methane gas to which 6% hydrogen ($H_2$) was added (Add) to have a methane to hydrogen molar ratio of 100:6.2; and a methane gas to which 3% carbonic acid gas ($CO_2$) was added (Add) to have a methane to carbonic acid gas ($CO_2$) molar ratio of 100:3.

FIG. 5 is a graph showing a time variation in the carbon formation rate, in which each of the catalysts relating to Comparative Example 1 and to Example 1 was reacted with each reaction gas of: a 100% methane gas; a methane gas to which 6% hydrogen was added to have a methane to hydrogen molar ratio of 100:6.2; and a methane gas to which 3% carbonic acid gas was added to have a methane to carbonic acid gas ($CO_2$) molar ratio of 100:3.

As apparent from property illustrations of FIGS. 1 to 4, it is found that the catalyst loading not only molybdenum (Mo) but also copper (Cu) is equal to the catalyst loading molybdenum (Mo) alone, in methane conversion rate, benzene formation rate, naphthalene formation rate and BTX formation rate, in the reaction with the 100% methane gas and the reaction with the 6.2% hydrogen-added methane gas. Additionally, the effect derived from loading copper (Cu) is hardly shown in the reaction with the 100% methane gas and the reaction with the 6.2% hydrogen-added methane gas.

On the other hand, it is found, in the reaction with the 3% carbonic acid gas-added methane gas, that the catalyst loading not only molybdenum (Mo) but also copper (Cu) is more improved than the catalyst loading molybdenum (Mo) alone in activity life of the methane conversion rate, the benzene formation rate, the naphthalene formation rate and the BTX formation rate.

More specifically, the catalyst loading copper (Cu) in addition to molybdenum (Mo) is found to be remarkably improved in activity life of the methane conversion rate, the benzene formation rate, the naphthalene formation rate and the BTX formation rate, in the reaction with the carbonic acid-containing methane gas. Further, it is confirmed by the property illustration of FIG. 5 that the catalyst is remarkably reduced in carbon formation rate when reacted with the carbonic acid-containing methane gas.

Then, verifications were made on a time variation in the methane conversion rate, the benzene formation rate, the naphthalene formation rate, the BTX formation rate and the carbon formation rate, in cases where each catalyst of Comparative Examples 1 to 3 and Example 1 was reacted with methane and carbonic acid gas. A method for verification will be discussed below.

14 g of a catalyst (having a zeolite ratio of 82.50%) serving as a target for evaluation was charged into a reaction pipe of a fixed-bed flow reactor (the pipe had an internal diameter of 18 mm and was produced in such a manner as to make a calorizing treatment on Inconel 800H's portion with which gas is to be brought into contact). Then, a carbonic acid gas-added methane gas (having a methane to carbonic acid gas ($CO_2$) molar ratio of 100:3) was supplied to the reaction pipe, as a reaction gas. The catalyst was thus reacted with the reaction gas under the conditions of: 3000 ml/g–ZSM-5/h ($CH_4$ gas flow base) of reaction space velocity; 780° C. of reaction temperature; 24 hours of reaction time; and 0.3 MPa of reaction pressure. During the reaction, a product analysis was conducted to examine a time variation in the methane conversion rate, the hydrogen formation rate, the benzene formation rate, the naphthalene formation rate, the BTX formation rate and the carbon formation rate. The product analysis was carried out by using TCD-GC and FID-GC.

Figure 6:
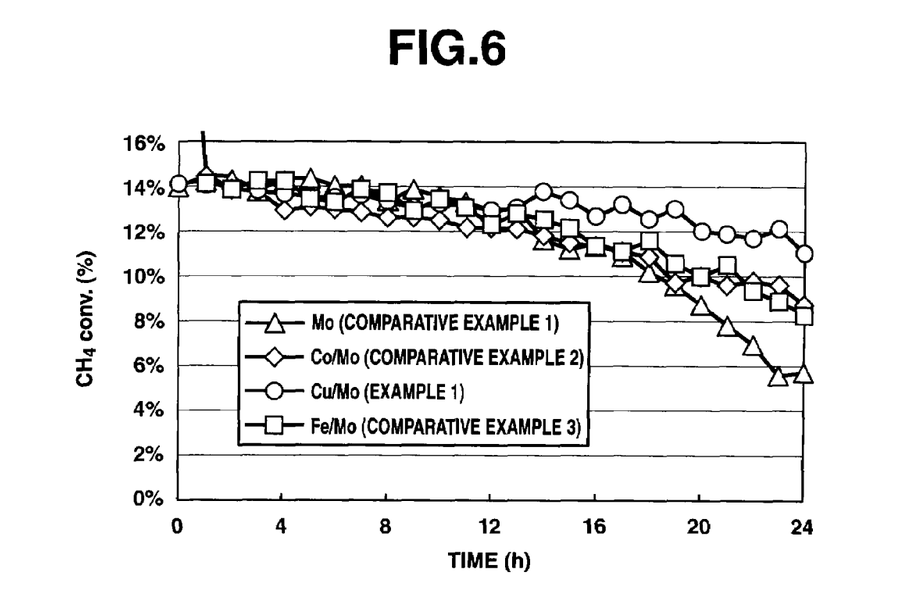
FIG. 6 is a graph showing a time variation in the methane conversion rate in cases where each catalyst of Comparative Examples 1 to 3 and Example 1 was reacted with methane and carbonic acid gas.

FIG. 6 is a graph showing a time variation in the methane conversion rate in cases where each catalyst of Comparative Examples 1 to 3 and Example 1 was reacted with methane and carbonic acid gas. It is apparent from this time variation in the methane conversion rate, as shown in this property illustration, that the catalyst of Example 1 (or the catalyst loading molybdenum and copper (Cu/Mo)) is improved in activity life stability of the methane conversion rate, as compared with conventional techniques such as the catalyst of Comparative Example 1 (or the catalyst loading molybdenum alone (Mo)), the catalyst of Comparative Example 2 (or the catalyst loading molybdenum and cobalt (Co/Mo)) and the catalyst of Comparative Example 3 (or the catalyst loading molybdenum and iron (Fe/Mo)).

Figure 7:
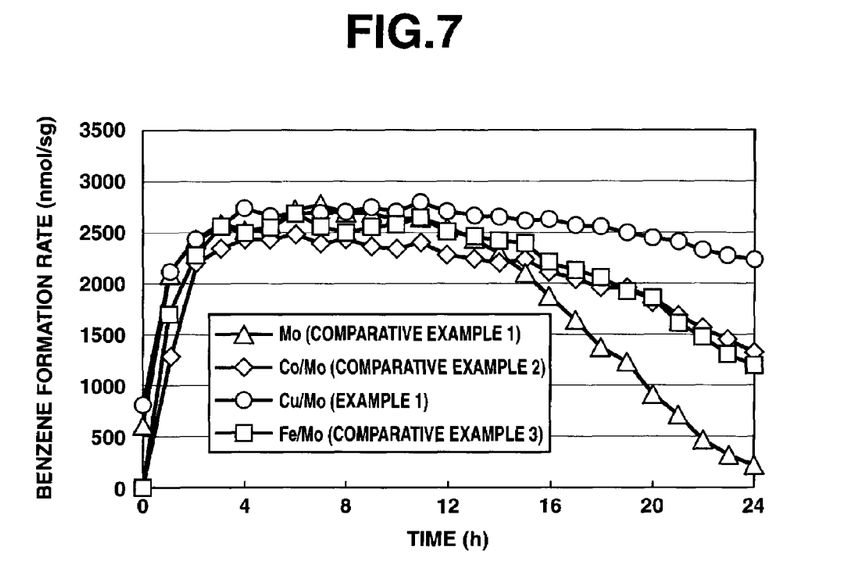
FIG. 7 is a graph showing a time variation in the benzene formation rate in cases where each catalyst of Comparative Examples 1 to 3 and Example 1 was reacted with methane and carbonic acid gas.

FIG. 7 is a graph showing a time variation in the benzene formation rate in cases where each catalyst of Comparative Examples 1 to 3 and Example 1 was reacted with methane and carbonic acid gas. It is apparent from this property illustration that the catalyst of Example 1 (Cu/Mo) is improved in activity life stability of the benzene formation rate, as compared with conventional techniques such as the catalyst of Comparative Example 1 (Mo), the catalyst of Comparative Example 2 (Co/Mo) and the catalyst of Comparative Example 3 (Fe/Mo).

Figure 8:
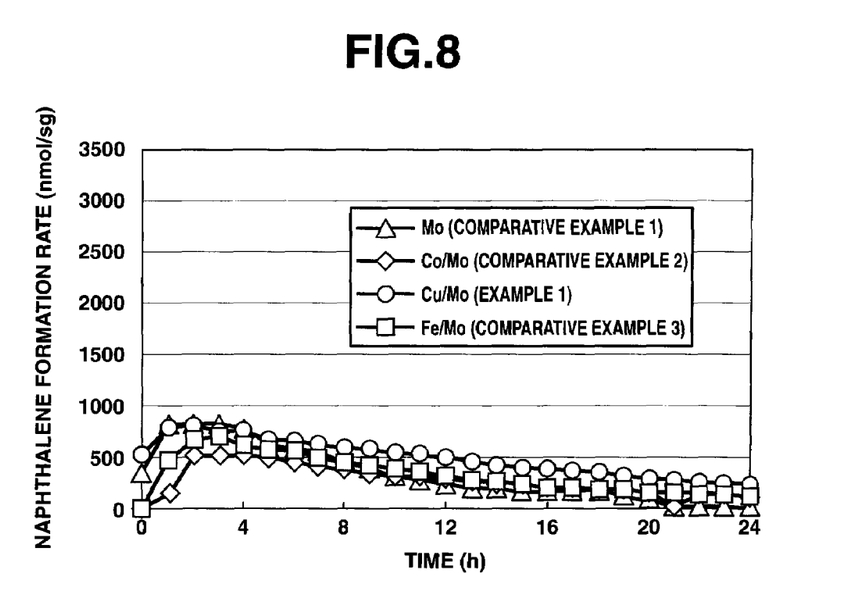
FIG. 8 is a graph showing a time variation in the naphthalene formation rate in cases where each catalyst of Comparative Examples 1 to 3 and Example 1 was reacted with methane and carbonic acid gas.

FIG. 8 is a graph showing a time variation in the naphthalene formation rate in cases where each catalyst of Comparative Examples 1 to 3 and Example 1 was reacted with methane and carbonic acid gas. It is apparent from this property illustration that the catalyst of Example 1 (Cu/Mo) is improved in activity life stability of the naphthalene formation rate, as compared with conventional techniques such as the catalyst of Comparative Example 1 (Mo), the catalyst of Comparative Example 2 (Co/Mo) and the catalyst of Comparative Example 3 (Fe/Mo).

Figure 9:
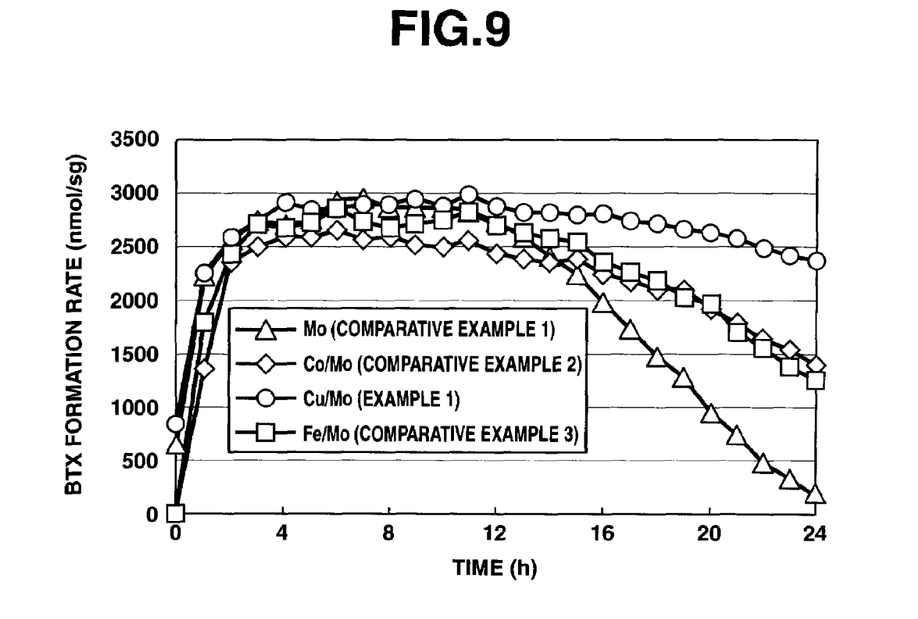
FIG. 9 is a graph showing a time variation in the BTX formation rate in cases where each catalyst of Comparative Examples 1 to 3 and Example 1 was reacted with methane and carbonic acid gas.

FIG. 9 is a graph showing a time variation in the BTX formation rate in cases where each catalyst of Comparative Examples 1 to 3 and Example 1 was reacted with methane and carbonic acid gas. It is apparent from this property illustration that the catalyst of Example 1 (Cu/Mo) is improved in activity life stability of the BTX formation rate, as compared with conventional techniques such as the catalyst of Comparative Example 1 (Mo), the catalyst of Comparative Example 2 (Co/Mo) and the catalyst of Comparative Example 3 (Fe/Mo).

Figure 10:
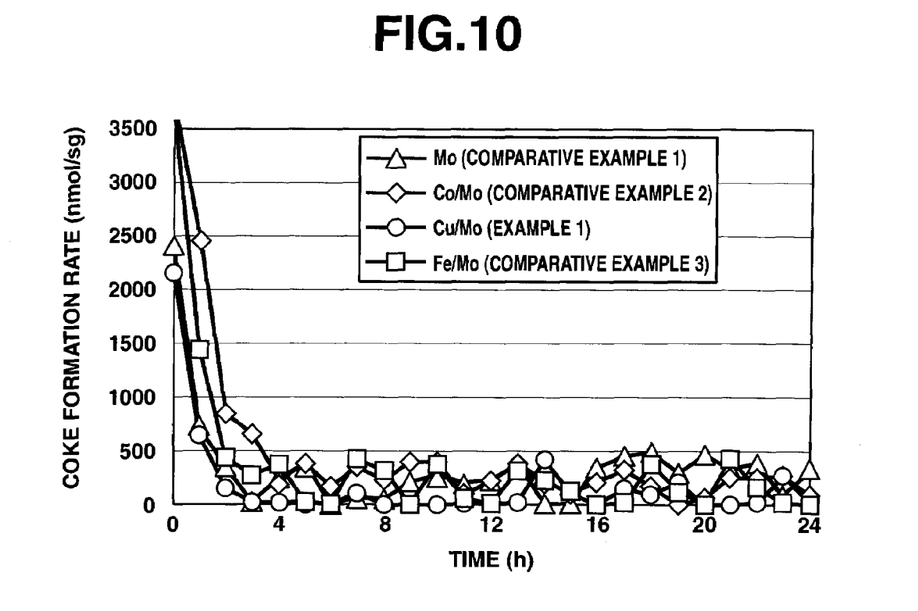
FIG. 10 is a graph showing a time variation in the carbon formation rate in cases where each catalyst of Comparative Examples 1 to 3 and Example 1 was reacted with methane and carbonic acid gas.

FIG. 10 is a graph showing a time variation in the carbon formation rate in cases where each catalyst of Comparative Examples 1 to 3 and Example 1 was reacted with methane and carbonic acid gas. It is apparent from this property illustration that the catalyst of Example 1 (Cu/Mo) is reduced in carbon formation rate, as compared with conventional techniques such as the catalyst of Comparative Example 1 (Mo), the catalyst of Comparative Example 2 (Co/Mo) and the catalyst of Comparative Example 3 (Fe/Mo).

As apparent from the above-mentioned results of Examples, the catalyst for producing aromatic compounds from lower hydrocarbons, formed by loading copper as a second metal component in addition to molybdenum on metallo-silicate, is confirmed to be improved in activity life stability of the methane conversion rate when reacted with lower hydrocarbons or carbonic acid gas. Further, it is found that the carbon formation rate which can cause catalytic activity reduction is decreased while making the activity life of the formation rate of BTX (which is useful components such as benzene and toluene) stable.

Then, the followings are Comparative Examples and Examples with which the dependence of a copper to molybdenum molar ratio in a case where molybdenum and copper were loaded on metallo-silicate was verified.

Example 2

A catalyst as Example 2 was formed loading copper and molybdenum thereon at a copper to molybdenum molar ratio of 0.1:1.0. It was produced by the same producing process (including the shaping process, the drying process, the calcining process and the carburization treatment) as the catalyst of Comparative Example 1, with the exception of the size of shaped substrate and the impregnation process.

In this shaping process, the mixed substance of the inorganic component, the organic binder and the water content relating to Comparative Example 1 was shaped by a vacuum extrusion machine into a rod (2.4 mm in diameter and 5 mm in length) at an extrusion pressure of 2 to 8 MPa. In an impregnation process, an impregnation solution prepared with copper acetate and ammonium molybdate was stirred. Then, the substrate shaped in the shaping process and including ZSM-5 was immersed in the stirred impregnation solution, thereby impregnating the shaped substrate with a molybdenum component and a copper component. This substrate was dried and then calcined in air, thereby obtaining a ZSM-5 substrate loading molybdenum and copper. In preparation of the impregnation solution, a loaded amount of molybdenum was set to be 6 wt. % based on the total amount of calcined substrate, while a loaded amount of copper was set to have a copper to molybdenum molar ratio of 0.1:1.0.

Example 3

A catalyst as Example 3 was formed loading copper and molybdenum thereon at a copper to molybdenum molar ratio of 0.3:1.0. It was produced by the same producing process (including the shaping process, the drying process, the calcining process and the carburization treatment) as the catalyst of Comparative Example 1, with the exception of the size of shaped substrate and the impregnation process.

In this shaping process, the mixed substance of the inorganic component, the organic binder and the water content relating to Comparative Example 1 was shaped by a vacuum extrusion machine into a rod (2.4 mm in diameter and 5 mm in length) at an extrusion pressure of 2 to 8 MPa. In an impregnation process, an impregnation solution prepared with copper acetate and ammonium molybdate was stirred. Then, the substrate shaped in the shaping process and including ZSM-5 was immersed in the stirred impregnation solution, thereby impregnating the shaped substrate with a molybdenum component and a copper component. This substrate was dried and then calcined in air, thereby obtaining a ZSM-5 substrate loading molybdenum and copper. In preparation of the impregnation solution, a loaded amount of molybdenum was set to be 6 wt. % based on the total amount of calcined substrate, while a loaded amount of copper was set to have a copper to molybdenum molar ratio of 0.3:1.0.

Example 4

A catalyst as Example 4 was formed loading copper and molybdenum thereon at a copper to molybdenum molar ratio of 0.45:1.0. It was produced by the same producing process (including the shaping process, the drying process, the calcining process and the carburization treatment) as the catalyst of Comparative Example 1, with the exception of the size of shaped substrate and the impregnation process.

In this shaping process, the mixed substance of the inorganic component, the organic binder and the water content relating to Comparative Example 1 was shaped by a vacuum extrusion machine into a rod (2.4 mm in diameter and 5 mm in length) at an extrusion pressure of 2 to 8 MPa. In an impregnation process, an impregnation solution prepared with copper acetate and ammonium molybdate was stirred. Then, the substrate shaped in the shaping process and including ZSM-5 was immersed in the stirred impregnation solution, thereby impregnating the shaped substrate with a molybdenum component and a copper component. This substrate was dried and then calcined in air, thereby obtaining a ZSM-5 substrate loading molybdenum and copper. In preparation of the impregnation solution, a loaded amount of molybdenum was set to be 6 wt. % based on the total amount of calcined substrate, while a loaded amount of copper was set to have a copper to molybdenum molar ratio of 0.45:1.0.

Example 5

A catalyst as Example 5 was formed loading copper and molybdenum thereon at a copper to molybdenum molar ratio of 0.6:1.0. It was produced by the same producing process (including the shaping process, the drying process, the calcining process and the carburization treatment) as the catalyst of Comparative Example 1, with the exception of the size of shaped substrate and the impregnation process.

In this shaping process, the mixed substance of the inorganic component, the organic binder and the water content relating to Comparative Example 1 was shaped by a vacuum extrusion machine into a rod (2.4 mm in diameter and 5 mm in length) at an extrusion pressure of 2 to 8 MPa. In an impregnation process, an impregnation solution prepared with copper acetate and ammonium molybdate was stirred. Then, the substrate shaped in the shaping process and including ZSM-5 was immersed in the stirred impregnation solution, thereby impregnating the shaped substrate with a molybdenum component and a copper component. This substrate was dried and then calcined in air, thereby obtaining a ZSM-5 substrate loading molybdenum and copper. In preparation of the impregnation solution, a loaded amount of molybdenum was set to be 6 wt. % based on the total amount of calcined substrate, while a loaded amount of copper was set to have a copper to molybdenum molar ratio of 0.6:1.0.

Example 6

A catalyst as Example 6 was formed loading copper and molybdenum thereon at a copper to molybdenum molar ratio of 0.8:1.0. It was produced by the same producing process (including the shaping process, the drying process, the calcining process and the carburization treatment) as the catalyst of Comparative Example 1, with the exception of the size of shaped substrate and the impregnation process.

In this shaping process, the mixed substance of the inorganic component, the organic binder and the water content relating to Comparative Example 1 was shaped by a vacuum extrusion machine into a rod (2.4 mm in diameter and 5 mm in length) at an extrusion pressure of 2 to 8 MPa. In an impregnation process, an impregnation solution prepared with copper acetate and ammonium molybdate was stirred. Then, the substrate shaped in the shaping process and including ZSM-5 was immersed in the stirred impregnation solution, thereby impregnating the shaped substrate with a molybdenum component and a copper component. This substrate was dried and then calcined in air, thereby obtaining a ZSM-5 substrate loading molybdenum and copper. In preparation of the impregnation solution, a loaded amount of molybdenum was set to be 6 wt. % based on the total amount of calcined substrate, while a loaded amount of copper was set to have a copper to molybdenum molar ratio of 0.8:1.0.

Evaluations were made on a time variation in the methane conversion rate, the benzene formation rate, the naphthalene formation rate and the BTX formation rate in cases where each catalyst of Examples 2 to 6 was reacted with methane and carbonic acid gas. A method for evaluation will be discussed below.

14 g of a catalyst (having a zeolite ratio of 82.50%) serving as a target for evaluation was charged into a reaction pipe of a fixed-bed flow reactor (the pipe had an internal diameter of 18 mm and was produced in such a manner as to make a calorizing treatment on Inconel 800H's portion with which gas is to be brought into contact). Then, a carbonic acid gas-added methane gas (having a methane to carbonic acid gas ($CO_2$) molar ratio of 100:3) was supplied to the reaction pipe, as a reaction gas. The catalyst was thus reacted with the reaction gas under the conditions of: 3000 ml/g–ZSM-5/h ($CH_4$ gas flow base) of reaction space velocity; 780° C. of reaction temperature; 24 hours of reaction time; and 0.3 MPa of reaction pressure. During the reaction, a product analysis was conducted to examine a time variation in the methane conversion rate, the benzene formation rate, the naphthalene formation rate and the BTX formation rate. The product analysis was carried out by using TCD-GC and FID-GC.

Figure 11:
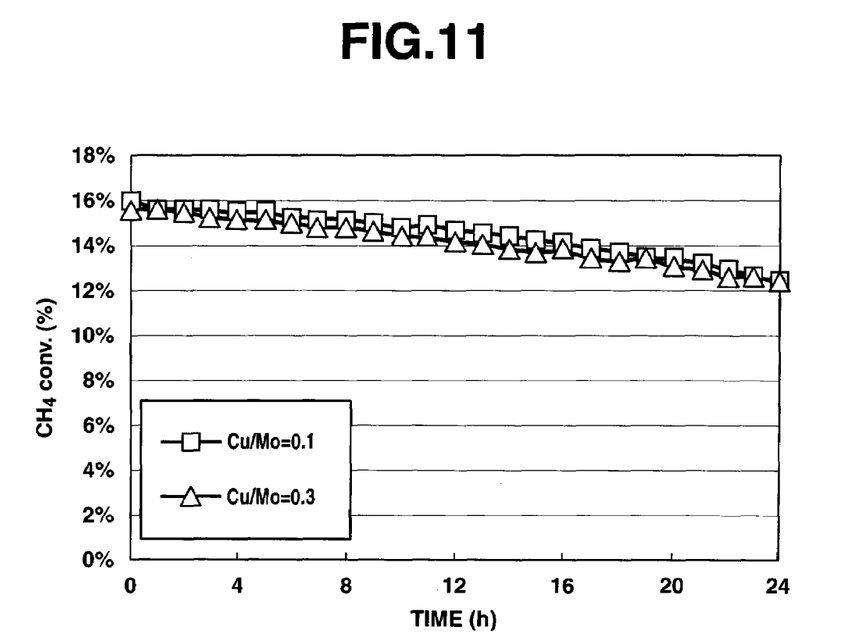
FIG. 11 is a graph showing a time variation in the methane conversion rate in cases where a carbonic acid gas-added methane gas having a methane to carbonic acid gas ($CO_2$) molar ratio of 100:3 was supplied to each of a catalyst (having a Cu to Mo molar ratio of 0.1) relating to Example 2 and a catalyst (having a Cu to Mo molar ratio of 0.3) relating to Example 3.

FIG. 11 is a graph showing a time variation in the methane conversion rate in cases where the evaluation method was applied to each of the catalyst (having a Cu to Mo molar ratio of 0.1) relating to Example 2 and the catalyst (having a Cu to Mo molar ratio of 0.3) relating to Example 3. It is apparent from this property illustration that both of the catalysts are improved in activity life stability of the methane conversion rate and maintained therein.

Figure 12:
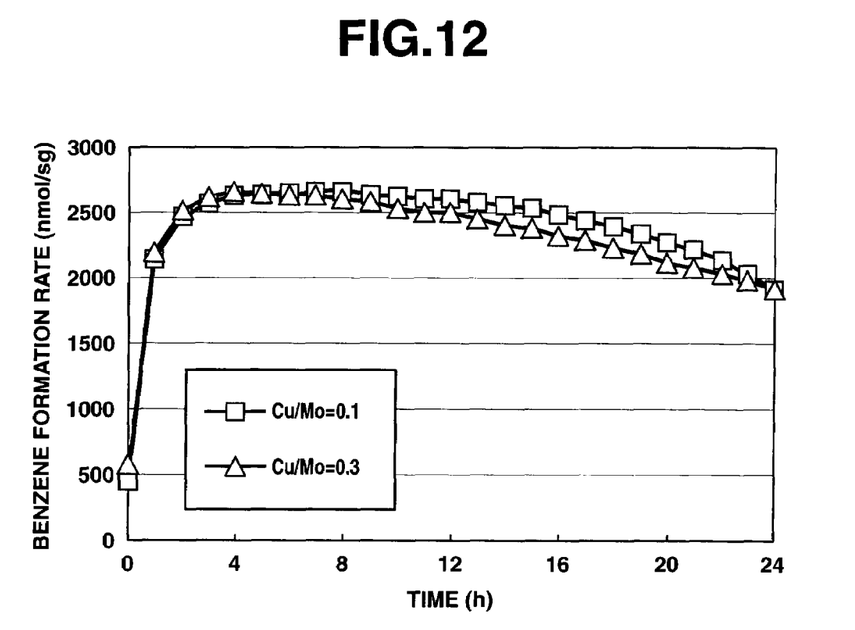
FIG. 12 is a graph showing a time variation in the benzene formation rate in cases where a carbonic acid gas-added methane gas having a methane to carbonic acid gas ($CO_2$) molar ratio of 100:3 was supplied to each of a catalyst (having a Cu to Mo molar ratio of 0.1) relating to Example 2 and a catalyst (having a Cu to Mo molar ratio of 0.3) relating to Example 3.

FIG. 12 is a graph showing a time variation in the benzene formation rate in cases where the evaluation method was applied to each of the catalyst (having a Cu to Mo molar ratio of 0.1) relating to Example 2 and the catalyst (having a Cu to Mo molar ratio of 0.3) relating to Example 3. It is apparent from this property illustration that both of the catalysts are improved in activity life stability of the benzene formation rate and maintained therein.

Figure 13:
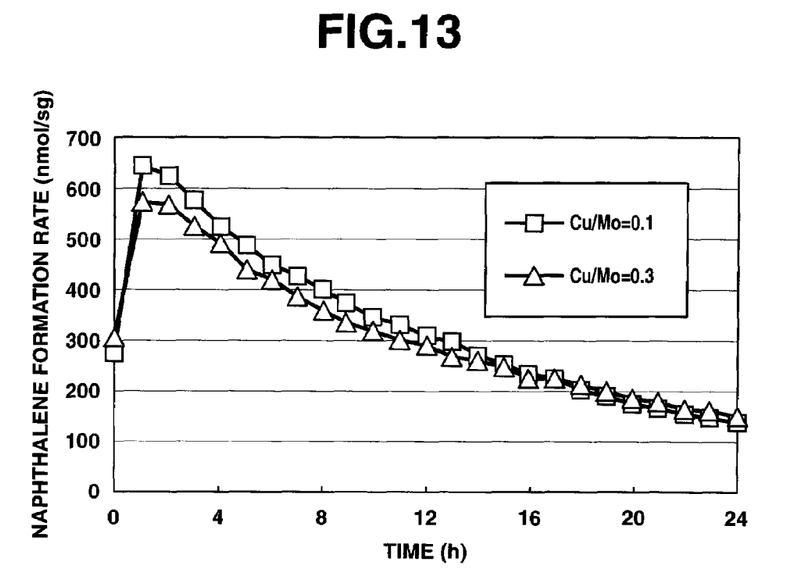
FIG. 13 is a graph showing a time variation in the naphthalene formation rate in cases where a carbonic acid gas-added methane gas having a methane to carbonic acid gas ($CO_2$) molar ratio of 100:3 was supplied to each of a catalyst (having a Cu to Mo molar ratio of 0.1) relating to Example 2 and a catalyst (having a Cu to Mo molar ratio of 0.3) relating to Example 3.

FIG. 13 is a graph showing a time variation in the naphthalene formation rate in cases where the evaluation method was applied to each of the catalyst (having a Cu to Mo molar ratio of 0.1) relating to Example 2 and the catalyst (having a Cu to Mo molar ratio of 0.3) relating to Example 3. It is apparent from this property illustration that both of the catalysts are improved in activity life stability of the naphthalene formation rate and maintained therein.

Figure 14:
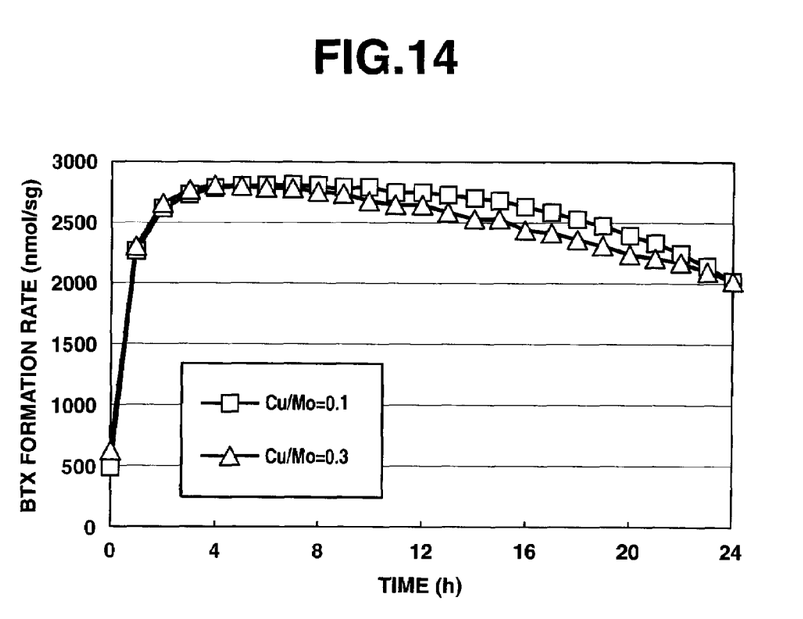
FIG. 14 is a graph showing a time variation in the BTX formation rate in cases where a carbonic acid gas-added methane gas having a methane to carbonic acid gas ($CO_2$) molar ratio of 100:3 was supplied to each of a catalyst (having a Cu to Mo molar ratio of 0.1) relating to Example 2 and a catalyst (having a Cu to Mo molar ratio of 0.3) relating to Example 3.

FIG. 14 is a graph showing a time variation in the BTX formation rate in cases where the evaluation method was applied to each of the catalyst (having a Cu to Mo molar ratio of 0.1) relating to Example 2 and the catalyst (having a Cu to Mo molar ratio of 0.3) relating to Example 3. It is apparent from this property illustration that both of the catalysts are improved in activity life stability of the BTX formation rate and maintained therein.

Table 1 shows the methane conversion rate, the benzene formation rate and the BTX formation rate of the catalysts of Examples 2 to 6 on which a reaction based on the above-mentioned evaluation method had made for 24 hours.

TABLE 1

|  | Example 2 | Example 3 | Example 4 | Example 5 | Example 6 |
| --- | --- | --- | --- | --- | --- |
| Molar ratio to Mo | Cu/Mo: 0.1 | Cu/Mo: 0.3 | Cu/Mo: 0.45 | Cu/Mo: 0.6 | Cu/Mo: 0.8 |
| Methane conversion rate (%) | 12.4 | 12.4 | 11.8 | 11.5 | 10.0 |
| Benzene formation rate (nmol/sg) | 1904.0 | 1897.1 | 1651.2 | 1469.9 | 990.6 |
| BTX formation rate (nmol/sg) | 2015.8 | 2031.1 | 1770.7 | 1575.0 | 1062.2 |

As apparent from Table 1, any of the catalysts of Examples 2 to 6 has the methane conversion rate of not less than 10%, the benzene formation rate of not less than 990 nmol/sg and the BTX formation rate of not less than 1000 nmol/sg, even after 24-hour reaction. With this, it is found that stability of the life of catalyst is maintained for a long period of time. Particularly, the benzene formation rate and the BTX formation rate in 24-hour reaction are higher in a case of using the catalysts of Examples 2 and 3 than in a case of using the catalysts of Examples 4 to 6. This means it is further preferable to load molybdenum and copper on metallo-silicate at a copper to molybdenum ratio of from 0.1 to 0.3, from the viewpoint of obtaining a catalytic function stability over a long period of time.

Concerning the dependence of a molar ratio to molybdenum of copper loaded after molybdenum, the lower the molar ratio of copper, the likelier the stability over a long period of time of the methane conversion rate, the benzene formation rate and the BTX production becomes excellent. Therefore, it is considered that the effect of stability of the catalytic activity life can be obtained even when the molar ratio of copper to molybdenum is less than 0.1 as a lower limit and when within a range of, for example, from 0.01 to 0.8.

Then, Examples for verifying effects obtained in a case where zeolite formed of metallo-silicate loaded molybdenum and copper after being treated with a silane compounds will be discussed.

Example 7

A catalyst as Example 7 was formed loading copper and molybdenum thereon at a copper to molybdenum molar ratio of 0.15:1.0, after treating a shaped substance with a silane compound to modify the substance with silane. It was produced by the same preparation and producing process as the catalyst of Comparative Example 1, with the exception of the size of shaped substrate and the impregnation process.

In this shaping process, the mixed substance of the inorganic component, the organic binder and the water content relating to Comparative Example 1 was shaped by a vacuum extrusion machine into a rod (2.4 mm in diameter and 5 mm in length) at an extrusion pressure of 2 to 8 MPa.

In a process of modification treatment with silane, APTES was dissolved in ethanol as a silane compound, in an addition amount of 0.5 wt. % based on the total amount of calcined catalyst. Thereafter, the substrate shaped in the shaping process relating to Comparative Example 1 so as to include ZSM-5 was impregnated with the ethanol for a certain period of time. This substrate was dried and then calcined at 550° C. for 6 hours, and thereafter treated with the silane compound to be modified with silane.

In an impregnation process, an impregnation solution prepared with copper acetate and ammonium molybdate was stirred. Then, the shaped substrate which underwent the process of modification treatment with silane was immersed in the stirred impregnation solution, thereby impregnating the shaped substrate with a molybdenum component and a copper component. This substrate was dried and then calcined in air, thereby obtaining a ZSM-5 substrate loading molybdenum and copper. In preparation of the impregnation solution, a loaded amount of molybdenum was set to be 6 wt. % based on the total amount of calcined substrate, while a loaded amount of copper was set to have a copper to molybdenum molar ratio of 0.15:1.0.

Example 8

A catalyst as Example 8 was formed loading copper and molybdenum thereon at a copper to molybdenum molar ratio of 0.3:1.0, after treating a shaped substance with a silane compound to modify the substance with silane. It was produced by the same producing process (including the shaping process, the drying process, the calcining process and the carburization treatment) as the catalyst of Comparative Example 1, with the exception of the size of shaped substrate and the impregnation process.

In this shaping process, the mixed substance of the inorganic component, the organic binder and the water content relating to Comparative Example 1 was shaped by a vacuum extrusion machine into a rod (2.4 mm in diameter and 5 mm in length) at an extrusion pressure of 2 to 8 MPa.

In a process of modification treatment with silane, APTES was dissolved in ethanol as a silane compound, in an addition amount of 0.5 wt. % based on the total amount of calcined catalyst. Thereafter, the substrate shaped in the shaping process relating to Comparative Example 1 so as to include ZSM-5 was impregnated with the ethanol for a certain period of time. This substrate was dried and then calcined at 550° C. for 6 hours, and thereafter treated with the silane compound to be modified with silane.

In an impregnation process, an impregnation solution prepared with copper acetate and ammonium molybdate was stirred. Then, the shaped substrate which underwent the process of modification treatment with silane was immersed in the stirred impregnation solution, thereby impregnating the shaped substrate with a molybdenum component and a copper component. This substrate was dried and then calcined in air, thereby obtaining a ZSM-5 substrate loading molybdenum and copper. In preparation of the impregnation solution, a loaded amount of molybdenum was set to be 6 wt. % based on the total amount of calcined substrate, while a loaded amount of copper was set to have a copper to molybdenum molar ratio of 0.3:1.0.

Example 9

A catalyst as Example 9 was formed loading copper and molybdenum thereon at a copper to molybdenum molar ratio of 0.45:1.0, after treating a shaped substance with a silane compound to modify the substance with silane. It was produced by the same producing process (including the shaping process, the drying process, the calcining process and the carburization treatment) as the catalyst of Comparative Example 1, with the exception of the size of shaped substrate and the impregnation process.

In this shaping process, the mixed substance of the inorganic component, the organic binder and the water content relating to Comparative Example 1 was shaped by a vacuum extrusion machine into a rod (2.4 mm in diameter and 5 mm in length) at an extrusion pressure of 2 to 8 MPa.

In a process of modification treatment with silane, APTES was dissolved in ethanol as a silane compound, in an addition amount of 0.5 wt. % based on the total amount of calcined catalyst. Thereafter, the substrate shaped in the shaping process relating to Comparative Example 1 so as to include ZSM-5 was impregnated with the ethanol for a certain period of time. This substrate was dried and then calcined at 550° C. for 6 hours, and thereafter treated with the silane compound to be modified with silane.

In an impregnation process, an impregnation solution prepared with copper acetate and ammonium molybdate was stirred. Then, the shaped substrate which underwent the process of modification treatment with silane was immersed in the stirred impregnation solution, thereby impregnating the shaped substrate with a molybdenum component and a copper component. This substrate was dried and then calcined in air, thereby obtaining a ZSM-5 substrate loading molybdenum and copper. In preparation of the impregnation solution, a loaded amount of molybdenum was set to be 6 wt. % based on the total amount of calcined substrate, while a loaded amount of copper was set to have a copper to molybdenum molar ratio of 0.45:1.0.

Example 10

A catalyst as Example 10 was formed loading copper and molybdenum thereon at a copper to molybdenum molar ratio of 0.6:1.0, after treating a shaped substance with a silane compound to modify the substance with silane. It was produced by the same producing process (including the shaping process, the drying process, the calcining process and the carburization treatment) as the catalyst of Comparative Example 1, with the exception of the size of shaped substrate and the impregnation process.

In this shaping process, the mixed substance of the inorganic component, the organic binder and the water content relating to Comparative Example 1 was shaped by a vacuum extrusion machine into a rod (2.4 mm in diameter and 5 mm in length) at an extrusion pressure of 2 to 8 MPa.

In a process of modification treatment with silane, APTES was dissolved in ethanol as a silane compound, in an addition amount of 0.5 wt. % based on the total amount of calcined catalyst. Thereafter, the substrate shaped in the shaping process relating to Comparative Example 1 so as to include ZSM-5 was impregnated with the ethanol for a certain period of time. This substrate was dried and then calcined at 550° C. for 6 hours, and thereafter treated with the silane compound to be modified with silane.

In an impregnation process, an impregnation solution prepared with copper acetate and ammonium molybdate was stirred. Then, the shaped substrate which underwent the process of modification treatment with silane was immersed in the stirred impregnation solution, thereby impregnating the shaped substrate with a molybdenum component and a copper component. This substrate was dried and then calcined in air, thereby obtaining a ZSM-5 substrate loading molybdenum and copper. In preparation of the impregnation solution, a loaded amount of molybdenum was set to be 6 wt. % based on the total amount of calcined substrate, while a loaded amount of copper was set to have a copper to molybdenum molar ratio of 0.6:1.0.

Evaluations were made on a time variation in the methane conversion rate, the benzene formation rate, the naphthalene formation rate and the BTX formation rate in cases where each catalyst of Examples 7 to 10 was reacted with methane and carbonic acid gas. A method for evaluation will be discussed below.

14 g of a catalyst (having a zeolite ratio of 82.50%) serving as a target for evaluation was charged into a reaction pipe of a fixed-bed flow reactor (the pipe had an internal diameter of 18 mm and was produced in such a manner as to make a calorizing treatment on Inconel 800H's portion with which gas is to be brought into contact). Then, a carbonic acid gas-added methane gas (having a methane to carbonic acid gas ($CO_2$) molar ratio of 100:3) was supplied to the reaction pipe, as a reaction gas. The catalyst was thus reacted with the reaction gas under the conditions of: 3000 ml/g-ZSM-5/h ($CH_4$ gas flow base) of reaction space velocity; 780° C. of reaction temperature; 24 hours of reaction time; and 0.3 MPa of reaction pressure. During the reaction, a product analysis was conducted to examine a time variation in the methane conversion rate, the benzene formation rate, the naphthalene formation rate and the BTX formation rate. The product analysis was carried out by using TCD-GC and FID-GC.

Figure 15:
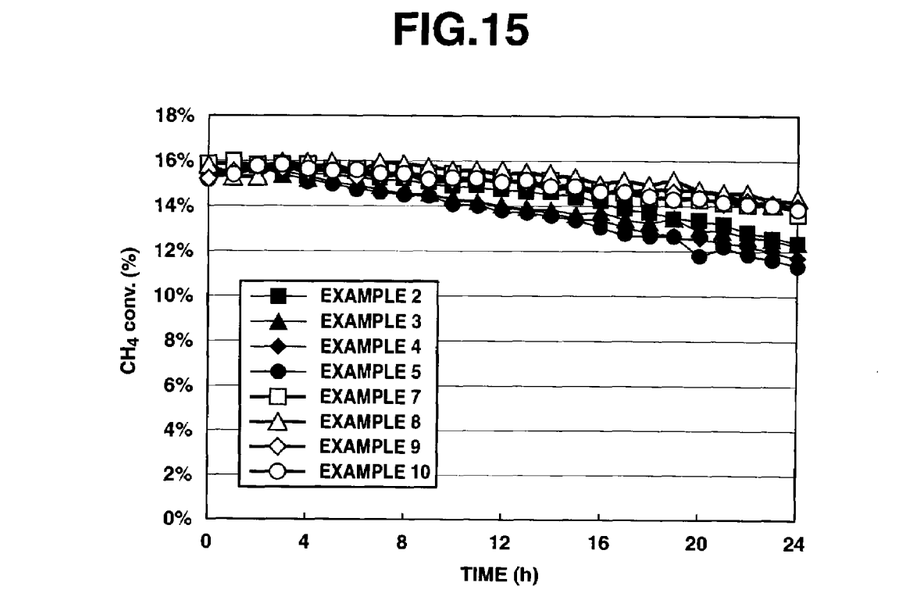
FIG. 15 is a graph showing a time variation in the methane conversion rate in cases where each catalyst of Examples 2 to 5 and 7 to 10 was reacted with a carbonic acid gas-added methane gas (having a methane to carbonic acid gas ($CO_2$) molar ratio of 100:3).

FIG. 15 is a graph showing a time variation in the methane conversion rate in cases where each catalyst of Examples 2 to 5 and 7 to 10 was reacted with a carbonic acid gas-added methane gas. As apparent from a comparison of the time variation of the methane conversion rate between the case where the catalysts of Examples 7 to 10 was reacted and the case where the catalysts of Examples 2 to 5 was reacted, the catalysts treated to be modified with silane as in Examples 7 to 10 are more improved in activity life stability of the methane conversion rate than those not treated with silane to be modified with silane as Examples 2 to 5.

Figure 16:
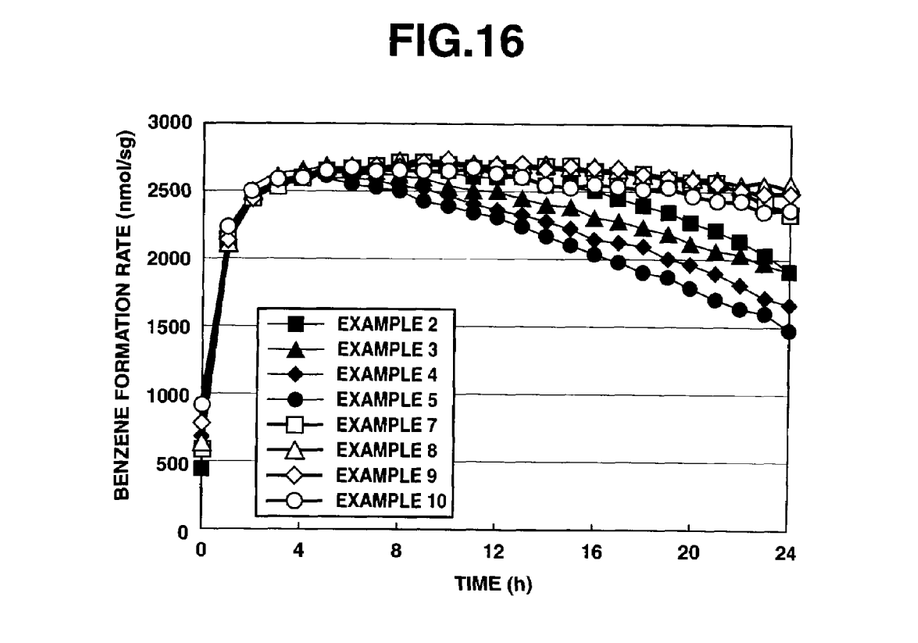
FIG. 16 is a graph showing a time variation in the benzene formation rate in cases where each catalyst of Examples 2 to 5 and 7 to 10 was reacted with a carbonic acid gas-added methane gas (having a methane to carbonic acid gas ($CO_2$) molar ratio of 100:3).

FIG. 16 is a graph showing a time variation in the benzene formation rate in cases where each catalyst of Examples 2 to 5 and 7 to 10 was reacted with a carbonic acid gas-added methane gas. As apparent from a comparison of the time variation of the benzene formation rate between the case where the catalysts of Examples 7 to 10 was reacted and the case where the catalysts of Examples 2 to 5 was reacted, the catalysts treated to be modified with silane as in Examples 7 to 10 are more improved in activity life stability of the benzene formation rate than those not treated with silane to be modified with silane as Examples 2 to 5.

Figure 17:
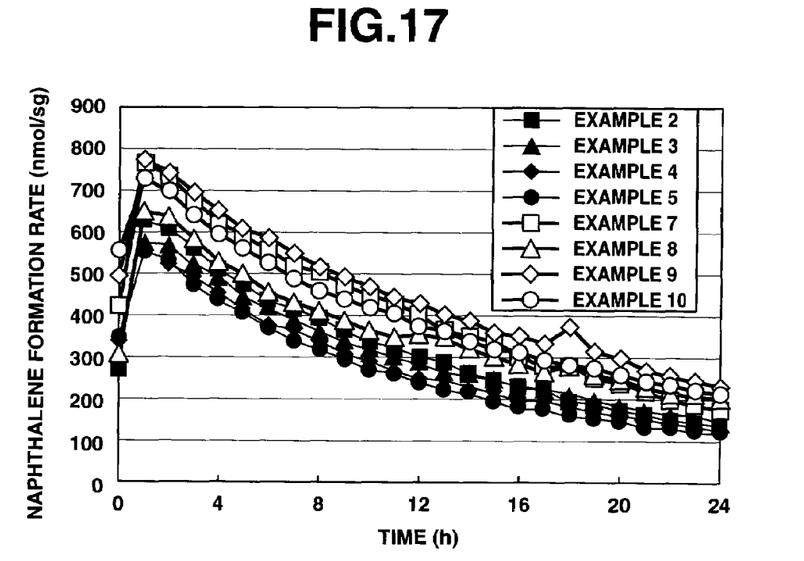
FIG. 17 is a graph showing a time variation in the naphthalene formation rate in cases where each catalyst of Examples 2 to 5 and 7 to 10 was reacted with a carbonic acid gas-added methane gas (having a methane to carbonic acid gas ($CO_2$) molar ratio of 100:3).

FIG. 17 is a graph showing a time variation in the naphthalene formation rate in cases where each catalyst of Examples 2 to 5 and 7 to 10 was reacted with a carbonic acid gas-added methane gas. As apparent from a comparison of the time variation of the naphthalene formation rate between the case where the catalysts of Examples 7 to 10 was reacted and the case where the catalysts of Examples 2 to 5 was reacted, the catalysts treated to be modified with silane as in Examples 7 to 10 are more improved in activity life stability of the naphthalene formation rate than those not treated with silane to be modified with silane as Examples 2 to 5.

Figure 18:
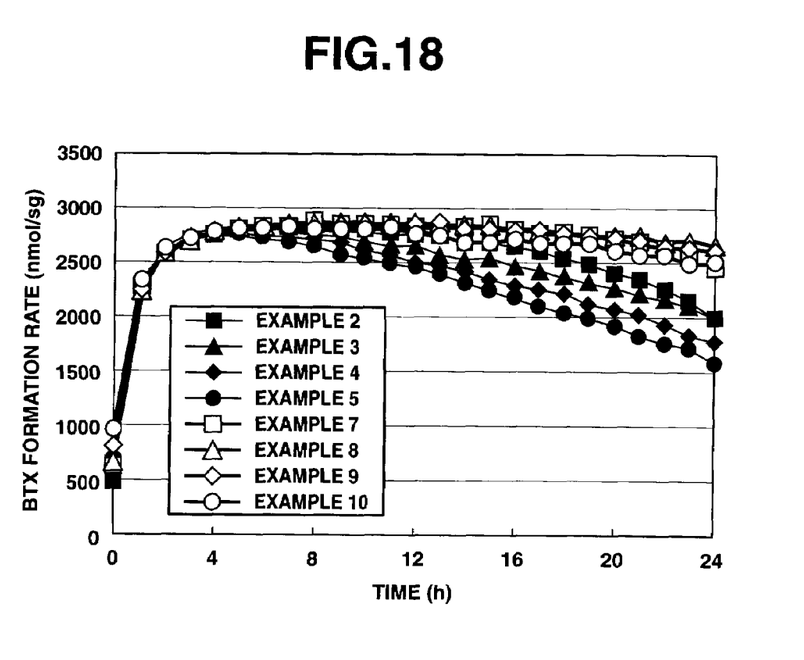
FIG. 18 is a graph showing a time variation in the BTX formation rate in cases where each catalyst of Examples 2 to 5 and 7 to 10 was reacted with a carbonic acid gas-added methane gas (having a methane to carbonic acid gas ($CO_2$) molar ratio of 100:3).

FIG. 18 is a graph showing a time variation in the BTX formation rate in cases where each catalyst of Examples 2 to 5 and 7 to 10 was reacted with a carbonic acid gas-added methane gas. As apparent from a comparison of the time variation of the BTX formation rate between the case where the catalysts of Examples 7 to 10 was reacted and the case where the catalysts of Examples 2 to 5 was reacted, the catalysts treated to be modified with silane as in Examples 7 to 10 are more improved in activity life stability of the BTX formation rate than those not treated with silane to be modified with silane as Examples 2 to 5.

Table 2 shows the methane conversion rate, the benzene formation rate, the naphthalene formation rate and the BTX formation rate in each of 3-hour reaction, 10-hour reaction and 24-hour reaction in which each catalyst of Examples 2 to 5 and 7 was reacted with carbonic acid gas-added methane gas. In comparisons among Examples and Comparative Examples, concerning activity property in each time period of reaction, and more particularly concerning activity property in 24-hour reaction, it is found that the catalysts treated to be modified with silane as Examples 8 to 10 are greater in methane conversion rate, benzene formation rate, naphthalene formation rate and BTX formation rate and in activity than those of: Examples 3 to 5 having an equal loaded amount of copper based on molybdenum; and Comparative Examples.

TABLE 2

|  | Methane conversion rate (%) | | | Benzene formation rate (nmol/sg) | | | Naphthalene formation rate (nmol/sg) | | | BTX formation rate (nmol/sg) | | |
| --- | --- | --- | --- | --- | --- | --- | --- | --- | --- | --- | --- | --- |
|  | 3 h | 10 h | 24 h | 3 h | 10 h | 24 h | 3 h | 10 h | 24 h | 3 h | 10 h | 24 h |
| Example 2 | 15.6 | 14.8 | 12.4 | 2574 | 2626 | 1904 | 574 | 344 | 139 | 2722 | 2786 | 2016 |
| Example 3 | 15.4 | 14.4 | 12.4 | 2613 | 2525 | 1897 | 523 | 317 | 149 | 2763 | 2682 | 2030 |
| Example 4 | 15.3 | 14.3 | 11.8 | 2560 | 2460 | 1651 | 491 | 290 | 121 | 2708 | 2615 | 1771 |
| Example 5 | 15.5 | 14.1 | 11.5 | 2571 | 2385 | 1470 | 469 | 269 | 118 | 2719 | 2537 | 1575 |
| Example 7 | 15.8 | 15.4 | 13.6 | 2557 | 2684 | 2318 | 674 | 444 | 166 | 2701 | 2846 | 2456 |
| Example 8 | 15.7 | 15.4 | 14.2 | 2619 | 2813 | 2597 | 603 | 378 | 208 | 2774 | 2987 | 2770 |
| Example 9 | 15.6 | 15.1 | 14.0 | 2563 | 2710 | 2453 | 694 | 469 | 228 | 2706 | 2869 | 2607 |
| Example 10 | 15.7 | 15.2 | 13.8 | 2578 | 2644 | 2352 | 746 | 697 | 610 | 2723 | 2799 | 2503 |

As discussed above, a catalyst according to the present invention is formed by treating metallo-silicate with silane to modify it with silane and then by loading molybdenum and copper on the metallo-silicate. With this, an activity life stability of the methane conversion rate is improved so that the benzene formation rate, the naphthalene formation rate and the BTX (useful components such as benzene and toluene) formation rate can be steadily obtained.

In the above-mentioned Examples, ZSM-5 was employed as metallo-silicate on which metal components are loaded; however, effects are provided equally to those in the above-mentioned Examples even when MCM-22 is employed. Further, a loaded amount of molybdenum was 6 wt. % based on the total amount of calcined catalyst, in the above-mentioned Examples; however, effects are provided equally to those in the above-mentioned Examples even when a loaded amount of molybdenum is within a range of from 2 to 12 wt. % based on the total amount of catalyst. Further, copper was loaded at a copper to molybdenum molar ratio of 0.15 to 0.6, in the above-mentioned Examples; however, effects are provided equally to those in the above-mentioned Examples even when the molar ratio is 0.01 to 0.8. Further, an addition amount of silane compounds was 0.5 wt. % based on the total amount of calcined catalyst, in the above-mentioned Examples; however, effects are provided equally to those in the above-mentioned Examples when an addition amount of silane compounds is less than 2.5 wt. % based on the total amount of calcined catalyst. Further, in the method for evaluating the above-mentioned Examples, the catalyst was reacted with a reaction gas having a methane to carbonic acid gas ($CO_2$) molar ratio of 100:3 in order to produce aromatic compounds; however, effects are provided equally to those in the above-mentioned Examples even when an addition amount of the carbonic acid gas is within a range of from 0.5 to 6 wt. % based on the total of the reaction gas.

What is claimed is:
1. A catalyst for producing an aromatic compound from a lower hydrocarbon, comprising:
a metallo-silicate serving as a substrate and calcined upon loading molybdenum and copper thereon, wherein the aromatic compound is produced by reacting the catalyst with the lower hydrocarbon and a carbonic acid gas, wherein the metallo-silicate comprises pores that are substantially 4.5 to 6.5 angstroms in diameter, wherein molybdenum and copper are loaded on the metallo-silicate at a copper to molybdenum molar ratio of 0.1 to 0.8.

2. A catalyst for producing an aromatic compound from a lower hydrocarbon, as claimed in claim 1, wherein a loaded amount of molybdenum is within a range of from 2 to 12 wt. % based on total amount of the calcined catalyst.

3. A catalyst for producing an aromatic compound from a lower hydrocarbon, as claimed in claim 1, wherein molybdenum and copper are loaded on the metallo-silicate at a copper to molybdenum molar ratio of 0.1 to 0.3.

4. A catalyst for producing an aromatic compound from a lower hydrocarbon, as claimed in claim 1, wherein the metallo-silicate is a zeolite.

5. A catalyst for producing an aromatic compound from a lower hydrocarbon, as claimed in claim 4, wherein molybdenum and copper are loaded on the zeolite after the zeolite is treated with a silane compound larger than a pore of the zeolite in diameter and having an amino group and a straight-chain hydrocarbon group, the amino group being able to selectively react with the zeolite at a Bronsted acid point of the zeolite.

6. A catalyst for producing an aromatic compound from a lower hydrocarbon, as claimed in claim 5, wherein the silane compound includes APTES (3-aminoproxyl-tri ethoxysilane).

7. A catalyst for producing an aromatic compound from a lower hydrocarbon, as claimed in claim 6, wherein the modification treatment with the silane compound is made in a manner that an addition amount of the APTES is less than 2.5 wt. % based on total amount of the calcined catalyst.

8. A catalyst for producing an aromatic compound from a lower hydrocarbon, as claimed in claim 7, wherein the modification treatment with the silane compound is made in a manner that an addition amount of the APTES is 0.5 wt. % based on total amount of the calcined catalyst.

9. A catalyst for producing an aromatic compound from a lower hydrocarbon, as claimed in claim 4, wherein a calcining temperature applied during the calcination made after molybdenum and copper are loaded on the zeolite is within a range of from 550 to 800° C.

10. A catalyst for producing an aromatic compound from a lower hydrocarbon, as claimed in claim 4, wherein the zeolite includes one of ZSM-5 and MCM-22.

11. A catalyst for producing an aromatic compound from a lower hydrocarbon, as claimed in claim 10, wherein the zeolite includes ZSM-5.

12. A method of using the catalyst, as claimed in claim 1, in the manufacture of an aromatic compound, comprising reacting the catalyst with a reaction gas containing a lower hydrocarbon and a carbonic acid gas to produce the aromatic compound.

13. A method, as claimed in claim 12, wherein an addition amount of the carbonic acid gas is within a range of from 0.5 to 6 wt. % based on a total of the reaction gas.

* * * * *